United States Patent [19]

Tseo

[11] Patent Number: 4,798,589
[45] Date of Patent: Jan. 17, 1989

[54] DIAPHRAGM PUMP CASSETTE

[75] Inventor: Gus G. Tseo, San Diego, Calif.

[73] Assignee: Fisher Scientific Group Inc., San Diego, Calif.

[21] Appl. No.: 62,488

[22] Filed: Jun. 15, 1987

[51] Int. Cl.⁴ .............................................. A61M 5/20
[52] U.S. Cl. ............................ 604/152; 128/DIG. 12; 92/98 D
[58] Field of Search ................... 604/65, 67, 151, 152, 604/153; 128/DIG. 12, DIG. 13; 92/96, 98 R, 98 D, 102

[56] References Cited

U.S. PATENT DOCUMENTS

| | | | |
|---|---|---|---|
| 2,954,738 | 10/1960 | DiVette . | |
| 3,079,946 | 3/1963 | Rösler | 92/98 R |
| 3,294,030 | 12/1966 | Fox | 92/98 D |
| 3,375,759 | 5/1966 | Smith . | |
| 3,492,968 | 2/1970 | Workman, Jr. | 92/98 R |
| 3,551,076 | 12/1970 | Wilson . | |
| 3,769,879 | 11/1973 | Lofquist, Jr. . | |
| 3,976,402 | 8/1976 | Lundquist | 604/152 |
| 3,985,133 | 11/1976 | Jenkins et al. . | |
| 3,993,061 | 11/1976 | O'Leary | 128/DIG. 12 |
| 3,995,723 | 12/1976 | Holcomb, Jr. | 92/98 D |
| 4,021,157 | 5/1977 | Elderfield . | |
| 4,396,385 | 8/1983 | Kelly et al. | 128/DIG. 12 |
| 4,403,924 | 9/1983 | Gebauer et al. . | |
| 4,456,009 | 6/1984 | Vcelka et al. . | |
| 4,515,591 | 5/1985 | Hemmerich et al. | 604/152 |
| 4,519,792 | 5/1985 | Dawe | 128/DIG. 12 |
| 4,658,585 | 4/1987 | Kamemoto et al. | 92/98 R |
| 4,682,533 | 7/1987 | Hafner et al. | 92/98 R |
| 4,684,367 | 8/1987 | Schaffer et al. | 128/DIG. 13 |

Primary Examiner—Stephen C. Pellegrino
Assistant Examiner—Ralph Lewis
Attorney, Agent, or Firm—Workman, Nydegger & Jensen

[57] ABSTRACT

The present invention is directed to an improved cassette for use in an intravenous infusion pump. The cassette of the present invention includes a cassette body which is capable of being removably secured within a volumetric pump. The cassette body has a volumetric chamber of predetermined volume which is placed in communication with an inlet and an outlet. The volumetric cassette includes an inlet corridor through which fluid may flow into the cassette. The inlet corridor in turn flows into a central corridor which leads directly to the volumetric chamber. The cassette also includes an outlet corridor which is also in communication with the central corridor and, in turn, the volumetric chamber. Fluid will, therefore, exit the volumetric chamber through the outlet corridor by way of the central corridor. The outlet corridor is then connected to the patient infusion line. The cassette of the present invention also includes a plunger which reciprocates within the interior of the volumetric chamber.

The present invention teaches the use of a diaphragm which covers the portion of the plunger which is exposed to the volumetric chamber. The diaphragm forms a friction seal with the exterior of the cassette body. The diaphragm is formed such that it reciprocates along with the plunger even though it is not securely attached to the plunger. As a result, when the plunger withdraws from the volumetric chamber, the diaphragm withdraws a corresponding distance. When the plunger again enters the volumetric chamber, the diaphragm enters as well.

8 Claims, 2 Drawing Sheets

DIAPHRAGM PUMP CASSETTE

BACKGROUND

1. Field of the Invention

The present invention is directed to a cassette for use in a volumetric infusion pump which is particularly adaptable for facilitating administration of fluids to a patient. More specifically, the present invention is related to a cassette which employs a diaphragm in order to seal the interior of the cassette from the outside environment and to facilitate operation of the cassette.

2. Background of the Invention

Various methods have been developed for the administration of fluids to a patient. This is particularly true with regard to intravenous administration of fluids. The most common method of administering such fluids is through the use of a standard intravenous ("IV") administration set. The use of such an intravenous administration set generally requires suspending a container of fluid at an elevated position with respect to the patient. The container is then placed in communication with the patient by way of a series of tubes and connections as needed and desired, and finally through a needle disposed within the patient's vein. The administration of fluid occurs by the operation of the hydrostatic head created by the elevated container which is communicated through the infusion line to the patient.

When administering fluids intravenously to a patient by any chosen method, it is important that the rate of administration and the total quantity of fluids administered be accurately controlled. In the case of the IV administration set, the fluid from the elevated container must generally pass through a drip chamber where the number of drops per minute provides an approximate estimate of the rate of flow of fluid to the patient. The medical personnel in charge of the administration must, therefore, frequently check the drip rate and the amount of fluid left in the bottle in order to provide the necessary control. When it is necessary to adjust the rate of flow, the drip rate must be manually adjusted. Likewise, in order to stop the administration of fluid when the proper quantity of fluid has been administered, it is necessary to manually terminate the flow. The frequent manual intervention by medical personnel in the process of intravenous fluid administration makes the process time consuming, costly, and not particularly accurate.

Another serious problem with conventional IV administration sets relates to introducing foreign substances to the patient. Because of the need for frequent manual supervision of the process, there is always the possibility that air will enter the system and subsequently be introduced to the patient's blood stream. The introduction of air through a patient's vein can have devastating results. Similarly, the frequent handling of the components of the IV set, along with the related need to replace tubing, fluid containers and the like, increases the possibility of infection.

In order to overcome some of the problems encountered with the standard IV administration set, numerous pump devices have been proposed and used in the art for pumping fluids to a patient. Some of these pump devices, for example, use electronics means to detect the drip rate in a drip chamber so that the rate of flow can automatically be adjusted.

Certain types of pumps may employ a chamber member to apply pressure to an IV tube and, thus, provide a positive pumping action to the fluid being administered to the patient. While in some settings it is found that this type of pump is desirable, its use is still limited in that the rate of pumping and volume pumped are not easily controlled.

Another type of pump which has been used eliminates the elevated bottle of fluid and uses in its place a large volumetric chamber. Fluid is pumped from the large volumetric chamber by slowly introducing a large piston into the chamber and correspondingly forcing fluid from the chamber. The rate of flow from the chamber is controlled so that the volume of fluid introduced to the patient and the flow rate are maintained within acceptable ranges. This type of pump also has several disadvantages. Such pumps are found to be costly and difficult to maintain. Further, if the rate of infusion is low, it is difficult to accurately control the rate of infusion from the large volumetric chamber.

An additional type of pump introduces fluid to a patient from a small volumetric chamber. Typically, a piston moves reciprocally within the small volumetric chamber drawing fluid into the chamber as the piston withdraws from the chamber and then forcing fluid out of the chamber as the piston re-enters the chamber. One such pump is disclosed in U.S. Pat. No. 3,985,133 to Jenkins, et al. (Oct. 12, 1976). In that type of volumetric infusion pump, fluid from a conventional container flows into the device through an inlet line. In order to facilitate the flow of fluid into the device, the fluid container is generally elevated with respect to the pump. The fluid is pumped as described above and then leaves the pump through an outlet line for introduction to a patient.

In this type of pump, a removable "cassette" may be inserted into the pump during operation. The cassette includes a chamber of a predetermined volume, as well as a plunger piston which reciprocates within the chamber. The cassette operates on the same general principle as a conventional syringe with the plunger piston pulling fluid into the chamber as it is withdrawn from the chamber, and then subsequently forcing fluid back out of the chamber. The pump generally includes a drive means which is coupled to the plunger to control the pumping action so that fluid will enter and leave the cassette at a predetermined rate. One type of drive means is a stepping motor which is set at a controlled rate in accordance with the number of pulses required to pump the desired volume.

The volume of the chamber in the cassette is relatively small compared with the volume of fluid which is normally infused. This provides for precise control of the amount of fluid infused and the rate of infusion. At the same time the small size allows the cassette to be manufactured and sold relatively inexpensively. Such a cassette can, for example, be presterilized and disposable.

Using such an apparatus, the pump itself never comes in contact with fluid infused, so that the pump does not need to be sterilized after each use. The pump can be used repeatedly and only the cassette needs to be replaced. Further, it is only necessary to be concerned about the sterile condition of the cassette portion of the apparatus and the associated inlet and outlet lines.

In use, the cassette is supported on the pump so that a drive means of the pump engages an extension of the cassette plunger. Tubing is connected from the fluid reservoir to an inlet corridor of the cassette so that fluid may be introduced into the interior of the cassette as the plunger withdraws from the interior of the volumetric chamber. As was mentioned above, once the chamber is filled with the desired volume of fluid, the direction of the plunger reverses and re-enters the volumetric chamber, forcing fluid out an outlet corridor. The direction of flow of fluid into and out of the cassette is controlled by a two-way valve so that when the plunger is withdrawing from the interior of the volumetric chamber, fluid flows into the chamber, and while the plunger again proceeds into the volumetric chamber fluid is directed out the outlet corridor and toward the patient.

While this device has many desirable features, several problems remain. One of the primary problems relates to the means of sealing between the cassette body and the plunger. It will be appreciated that an effective seal is required in order to prevent fluid leakage from the volumetric chamber. Various means of sealing have been attempted but have been found to be less than satisfactory. Such means include the providing of an O-ring around the base of the cassette body at the intersection of the plunger. Likewise, it may be possible to simply provide close fitting engagement between the plunger and the cassette body (together with a flexible material along part of the plunger) such that sealing engagement may be obtained. It will be appreciated, however, that even using these means, leakage may be a problem. The plunger must reciprocate rapidly and continuously within the cassette body. As a result, fatigue and wear are often encountered which may result in failure of the seal.

A further problem encountered in the art is that of contamination of the interior of the volumetric chamber. Since the fluid flowing through the volumetric chamber will likely be introduced directly into the bloodstream of a patient, it is necessary to scrupulously maintain a sterile environment. It is particularly important to provide a bacterial seal, as well as a liquid seal, between the exterior environment and the interior of the volumetric chamber. The sealing means used to date for sealing the plunger and the volumetric chamber have been inadequate in providing such a bacterial seal. Simple O-rings or friction engagement will likely allow bacteria to enter the chamber by traveling in what is essentially a straight line. No effective barrier is provided.

From the above discussion it is apparent that what is currently needed in the art are improved means for sealing the volumetric cassette from the outside environment. It would be an advancement in the art to provide such sealing means which provided an improved liquid seal and at the same time, was able to withstand the repeated reciprocating movement of the plunger within the volumetric chamber. It would also be an advancement in the art to provide such sealing means which was extremely low cost so that the sealing means, along with the entire cassette, could be presterilized and disposable if desired. It would be a further advancement in the art to provide such sealing means which provided an effective block against bacterial intrusion into the interior of the volumetric chamber.

Such methods and apparatus are disclosed and claimed below.

BRIEF SUMMARY AND OBJECTS OF THE INVENTION

The present invention is directed to an improved cassette for use in an IV infusion pump of the type described above. In particular, the present invention is related to an improved cassette which includes a relatively small volumetric chamber and a reciprocating plunger which drives fluid through the volumetric chamber. The present invention also provides an improved means of sealing the plunger and the volumetric chamber.

The cassette of the present invention includes a cassette body of the general type described in U.S. Pat. No. 3,985,133 to Jenkins, which is capable of being removably secured within a volumetric pump. The cassette body has a volumetric chamber of predetermined volume which is placed in communication with an inlet and an outlet. The volumetric cassette includes an inlet corridor through which fluid may flow into the cassette. The inlet corridor in turn flows into a central corridor which leads directly to the volumetric chamber. The cassette also includes an outlet corridor which is also in communication with the central corridor and, in turn, the volumetric chamber. Fluid will, therefore, exit the volumetric chamber through the outlet corridor by way of the central corridor. The outlet corridor is then connected to the patient infusion line.

The cassette of the present invention also includes a two-way valve which controls flow into and out of the cassette. The two-way valve is disposed generally at the intersection between the inlet corridor and the outlet corridor. The direction of fluid travel can be easily controlled. When fluid flows into the cassette, the valve opens the connection between the inlet corridor and the central corridor leading to the volumetric chamber. When fluid is pumped out of the cassette, the valve opens the connection between the outlet corridor and the central corridor.

As discussed above, the cassette of the present invention also includes a plunger which reciprocates within the interior of the volumetric chamber. Thus, as the plunger pulls out of the volumetric chamber, fluid flows through the inlet corridor, past the two-way valve, through the central corridor and into the volumetric chamber. When the plunger reverses its direction and again moves upwardly through the volumetric chamber, fluid leaves the volumetric chamber through the central corridor past the two-way valve and out the outlet corridor. The outlet corridor is in turn placed in communication with the patient infusion line.

One of the important aspects of the present invention is the means for providing a seal between the interior of the volumetric chamber and the plunger. The present invention teaches the use of a diaphragm which covers the portion of the plunger which is exposed to the volumetric chamber. The diaphragm also forms a friction seal with the exterior of the cassette body. The diaphragm is formed such that it reciprocates along with the plunger. As a result, when the plunger withdraws from the volumetric chamber, the diaphragm withdraws a corresponding distance. When the plunger again enters the volumetric chamber, the diaphragm enters as well.

A further important feature of the diaphragm is that it provides a bacterial seal as well as a liquid seal. The diaphragm slides onto the base of the volumetric chamber in such a manner as to provide a friction of interference seal. In order to provide such a seal, the diaphragm must loop around the base of the volumetric chamber forming a cuff. In essence, the diaphragm cuff changes directions in order to seat on the base of the volumetric chamber. This change of direction provides an effective bacterial seal because bacteria are generally unable to travel by reversing their direction in this manner.

The present invention, therefore, provides an improvement on existing cassettes for use in IV pumps. The present invention includes vastly improved means of sealing the interior of the volumetric chamber from the exterior. The diaphragm of the present invention provides not only an effective liquid seal, but also an effective bacterial seal. In addition, the method of attaching the diaphragm to the remaining parts of the cassette is unique. The diaphragm simply provides an interference or friction attachment to both the plunger and the cassette body.

It is, therefore, a general object of the present invention to provide improved means for sealing the volumetric chamber of a volumetric cassette from the outside environment.

It is a further object of the present invention to provide an improved liquid seal which is able to withstand the reciprocating movement of the piston of such a cassette.

It is another object of the present invention to provide a diaphragm which provides such a liquid seal and also provides an effective block to the passage of bacteria into the interior of the volumetric chamber.

It is still another object of the present invention to provide an improved method of attaching the diaphragm to both the piston and the cassette body.

It is also an object of the present invention to provide an extremely low cost seal so that the cassette and sealing means may be presterilized and disposable if desired.

These and other objects of the invention will become apparent upon reading the following detailing description and appended claims, and upon reference to the accompanying drawings.

DETAILED DESCRIPTION OF THE PREFERRED EMBODIMENTS

Figure 1:
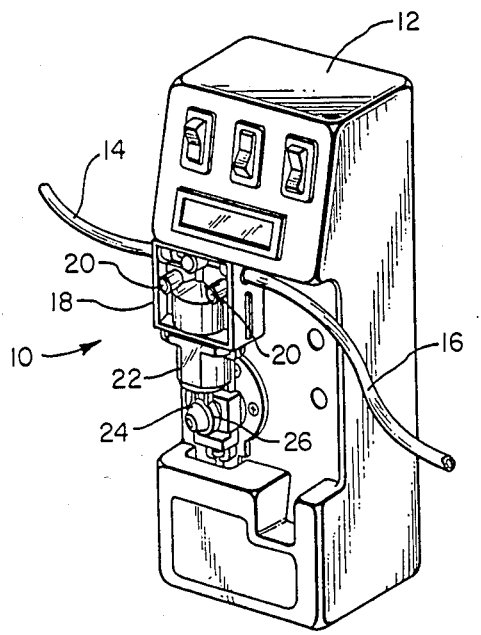
FIG. 1 is a perspective view illustrating the volumetric cassette of the present invention installed within an intravenous infusion pump.

The present invention can be best understood by reference to the drawings, wherein like parts are designated with like numerals throughout. Referring more particularly to FIG. 1, the volumetric cassette 10 of the present invention is illustrated in place in a standard intravenous infusion pump 12. The infusion pump 12 may be of the type which is known in the art, such as that disclosed in U.S. Pat. No. 3,985,133 to Jenkins et al. (Oct. 12, 1976). It will be appreciated that the present invention more specifically relates to the cassette for use in connection with such an infusion pump 12. The cassette has the capability of accepting relatively small volumes of fluid and then transmitting those small volumes to a patient in a controlled manner.

FIG. 1 illustrates an inlet line 14 and an outlet line 16 which provide for fluid flow through the volumetric cassette 10. Inlet line 14 is placed in communication with a source of fluid (not shown) for infusion into the patient. That source of fluid may be, for example, a standard IV bottle, or other similar type of reservoir of infusion fluid. Inlet line 14 is then securely attached to the volumetric cassette 10 by conventional means.

Outlet line 16, also illustrated in FIG. 1, is also securely attached to the cassette 10. The fluid which is introduced through inlet line 14 and then pumped by the infusion pump 12 leaves the volumetric cassette 10 through outlet line 16. Fluid leaving volumetric cassette 10 through outlet line 16 travels directly to the patient for infusion. Thus, outlet line 16 will likely be placed in direct communication with the circulatory system of a patient.

FIG. 1 also illustrates generally the cassette body 18. The cassette body 18 is securely, but removably, fastened to the infusion pump 12. Infusion pump 12 may be equipped with a plurality of shafts which fit securely within openings 20 in cassette body 18 in order to hold cassette body 18 in place during operation of infusion pump 12. Thus, the cassette body 18 can easily be placed into position and locked in place on infusion pump 12. Likewise, when infusion is complete the cassette body 18 can be easily removed and discarded.

FIG. 1 also generally illustrates the plunger 22 and the plunger shaft 24 of the volumetric cassette 10. As will be discussed in more detail below, plunger 22 reciprocates within the interior of cassette body 18. This provides the pumping action needed to cause fluid to travel in through inlet line 14 and out through outlet line 16.

Also illustrated is attachment member 26. Attachment member 26 allows for secure attachment between the plunger shaft 24 and the motor of the infusion pump 12. Thus, the infusion pump 12 can provide reciprocating movement to the plunger 24 to facilitate operation of the device.

Figure 2:
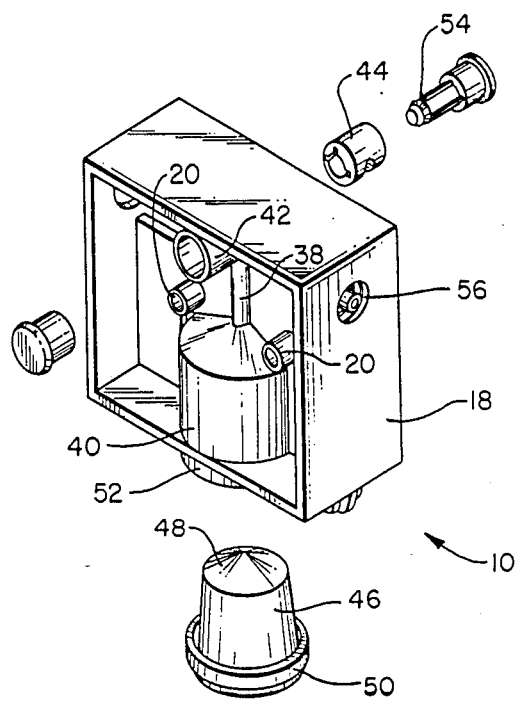
FIG. 2 is a perspective view of the cassette of the present invention.
Figure 2:
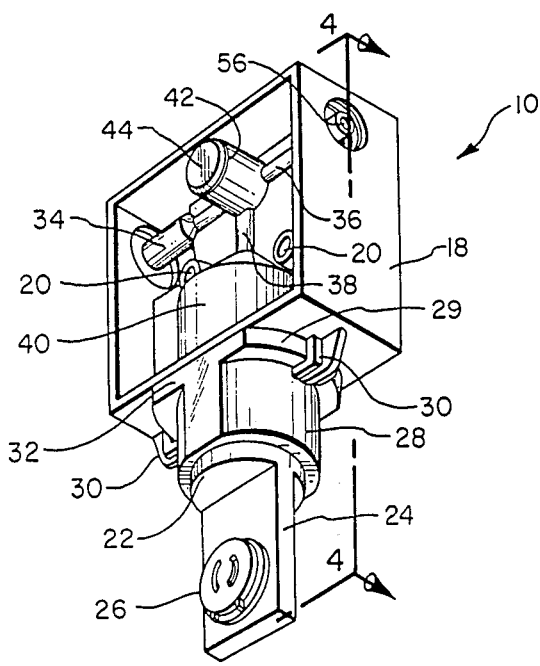

FIG. 2 illustrates the volumetric cassette of the present invention apart from the infusion pump 12. FIG. 2 illustrates the attachment member 26 which can be securely attached to the motor of the infusion pump 12 as described above. It will be appreciated from FIG. 2 that attachment member 26 allows the infusion motor of the infusion pump 12 to be placed in direct communication with plunger shaft 24, which in turn is securely attached to plunger 22. Thus, the motor of the infusion pump 12 is placed in direct mechanical communication with the plunger 22.

Also illustrated in FIG. 2 is diaphragm casing 28. Diaphragm casing 28 encases and secures in place the diaphragm 46 of volumetric cassette 10, when the volumetric cassette 10 is in operation. As shown in FIG. 2, diaphragm casing 28 may simply slide over the exterior of plunger 22 and then be secured to cassette body 18 by any known and acceptable means. One such means would be to provide prongs 30 on cassette body 18. Diaphragm casing 28 is then provided with a twist ring 29 having two flattened surfaces 32 so that the twist ring 29 may slide between prongs 30 if the flattened surfaces 32 face prongs 30. When the diaphragm casing 28 is seated in place with the twist ring 29 disposed beneath prongs 30, diaphragm casing 28 is rotated 90° such that prongs 30 engage the twist ring 29 and hold diaphragm casing 28 securely in place.

The exterior outlines of the fluid chambers and corridors of volumetric cassette 10 are also illustrated in FIG. 2. These include an inlet corridor 34 and an outlet corridor 36, with a central corridor 38 in the center of the cassette body 18. Central corridor 38 is, in turn, in communication with volumetric chamber 40, the exterior of which is illustrated in FIG. 2. The cassette body 18 includes a casing 42 for a two-way valve.

Figure 4:
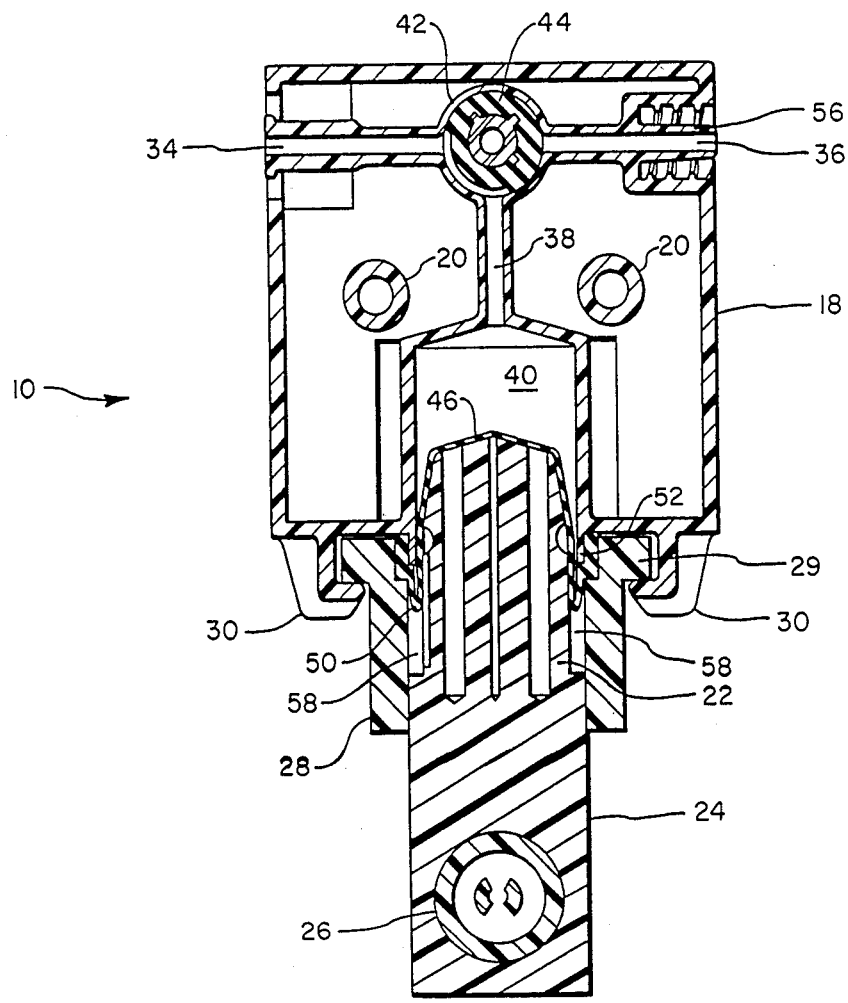
FIG. 4 is a cross-sectional plan view of the volumetric cassette of the present invention as seen along the line 4—4 in FIG. 2.

While the operation of these various fluid corridors will be understood more fully with reference to FIG. 4, the operation can be generally understood with reference to FIG. 2. Specifically, fluid enters the cassette body 18 through inlet corridor 34. The two-way valve 44 directs the incoming fluid down central corridor 38 into volumetric chamber 40. Upon completion of the intake stroke, two-way valve 44 is rotated to establish a pathway for fluid communication between volumetric chamber 40 and outlet corridor 36. Subsequently, when plunger 22 reverses its direction and again moves upwardly into volumetric chamber 40, fluid is forced out of volumetric chamber 40, up through central corridor 38, past two-way valve 44 and out outlet corridor 36.

Figure 3:
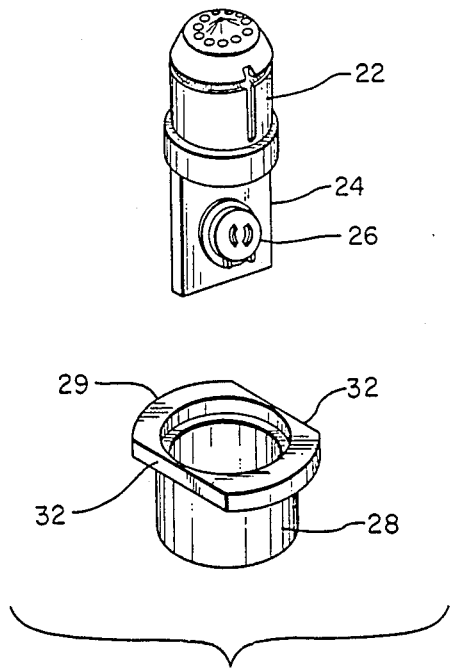
FIG. 3 is an exploded perspective view of the various components of the volumetric cassette of the present invention.

The structure of the plunger 22 and the diaphragm 46 can be appreciated more fully with reference to FIG. 3. FIG. 3 is an exploded view of the volumetric cassette 10. One unique feature of volumetric cassette 10 is the structure and function of diaphragm 46. Diaphragm 46 is generally cylindrical, or somewhat frustoconical, in shape. The upper end 48 of diaphragm 46 is totally enclosed. The lower end of diaphragm 46 terminates in a cuff 50 which forms the base of diaphragm 46. In essence, diaphragm 46 is folded upwardly at its base to form cuff 50.

In operation, the inside fold of cuff 50 slides within the interior of volumetric chamber 40 such that the outside of cuff 50 seats around base 52 of cassette body 18. Thus, an effective seal is created between the interior of volumetric chamber 40 and the exterior of the device. Cuff 50 not only provides a fluid seal but, because of the configuration of cuff 50, also prevents bacteria from traveling from the exterior of the cassette body 18 into the interior of volumetric chamber 40.

Diaphragm 46 is specifically formed to fit securely over the top of plunger 22. Indeed, a friction engagement is obtained between diaphragm 46 and plunger 22 such that the movement of plunger 22 causes corresponding movement of diaphragm 46 without the need for any further means of attachment. As plunger 22 is withdrawn from the interior of volumetric chamber 40, diaphragm 46 remains secured to plunger 22 and also withdraws. Likewise, when plunger 22 re-enters volumetric chamber 40 diaphragm 46 is also carried into the interior of the volumetric chamber 40.

It is important to note that the method of attachment of diaphragm 46 to plunger 22 and to base 52 of cassette body 18 is through friction attachment. There is no need for any further attachment means and none are provided. The only additional means for securing diaphragm 46 in place is diaphragm casing 28 which is secured around the exterior of cuff 50. Thus, diaphragm 46 can be easily installed and easily removed using a minimal number of parts. In addition, diaphragm 46 can be very easily manufactured by known methods and can in turn be attached to the device without significant effort.

FIG. 3 also illustrates motor shaft 54. Motor shaft 54 is a part of infusion pump 12 and operates the two-way valve 44. The movement of motor shaft 54 is coordinated with the portion of the infusion pump 12 which drives piston 22. Thus, as piston 22 is withdrawing from the interior of volumetric chamber 40, motor shaft 54 places two-way valve 44 in a position such that fluid can flow into volumetric chamber 40 through inlet corridor 44. Likewise, as the piston 22 again travels upwardly through volumetric chamber 40, motor shaft 54 places two-way valve 44 in a position such that fluid leaves cassette body 18 through outlet corridor 36.

An additional feature which is illustrated in both FIGS. 2 and 3 is outlet plug 56. Outlet plug 56 provides a means for attaching outlet line 16. Outlet line 16 is able to slide in place over outlet plug 56, providing a secure fluid tight attachment means.

The volumetric cassette 10 of the present invention can be better understood with reference to FIG. 4. FIG. 4 is a cross sectional view of the volumetric cassette 10. The important structural features of volumetric cassette 10, which were discussed generally above, are illustrated in cross section in FIG. 4.

It will be appreciated that a source of fluid will be placed in communication with inlet corridor 34 through a means, such as an inlet line 14 illustrated in FIG. 1. The fluid will flow along corridor 34 drawn by the negative pressure caused by the withdrawal of plunger 22 from volumetric chamber 40. As illustrated in FIG. 4, the fluid will flow past two-way valve 44, which is illustrated in position to allow fluid to flow into the device. The fluid will continue to travel through central corridor 38 into volumetric chamber 40.

When plunger 22 again travels upwardly into volumetric chamber 40 fluid is forced back up central corridor 38. Simultaneously with the up stroke of plunger 22, two-way valve 44 will have been rotated so that a clear path is formed for directing fluid out through outlet corridor 36. It will be appreciated that an outlet line 16 will be securely attached to outlet plug 56 in order to carry the fluid to its desired destination, specifically to a patient.

The diaphragm 46 is also illustrated in FIG. 4. Diaphragm 46 securely seats on top of plunger 22 through friction engagement and moves in response to movement of plunger 22. Also illustrated in FIG. 4 is cuff 50. It can be seen that cuff 50 provides a friction attachment with base 52 of cassette body 18.

As can be appreciated with reference to FIG. 4, a slight gap 58 exists between the interior of diaphragm casing 28 and the exterior of plunger 22. As plunger 22 is withdrawn from the interior of volumetric chamber 40, the gap 58 increases in size. The increase in size of gap 58 allows diaphragm 46 to roll and retract into the gap 58. Thus, smooth operation of the device is provided without binding diaphragm 46 in any way.

The cassette, diaphragm, and plunger of the present invention are all extremely inexpensive to manufacture and may be provided in a prepackaged and presterilized condition. As a result, once it is necessary to replace any or all of the parts, the existing parts may be disposed of easily and economically.

The cassette and the related parts will be made of materials which are both strong mechanically and which are chemically nonreactive. Specifically, it will be important to choose materials which do not react with the fluids which will likely be infused. Polymeric materials of the type generally used for medical applications are presently preferred for constructing the cassette body 18.

Likewise, it is necessary to choose appropriate materials for constructing the diaphragm 46. The diaphragm must be chemically compatible with the infusion fluids and must also be able to withstand the significant mechanical forces inherent in its operation. Materials which are presently preferred include flexible elastomeric materials of the type generally used in medical applications.

In view of the above description, it can be appreciated that all of the objects of the present invention have been accomplished by the volumetric cassette 10 of the present invention. The volumetric cassette 10 provides for a simple sealing means between the interior of the cassette and the exterior. That sealing means comprises diaphragm 46 which provides not only an effective fluid seal but also an effective bacterial seal. Bacteria are generally unable to change direction of travel in order to penetrate volumetric chamber 40 along the path defined by diaphragm 46. Thus, the cuff 50 of diaphragm 46 provides an effective bacterial seal.

The diaphragm 46 also provides an effective liquid seal between the interior of the cassette body 18 and the plunger 22. This is accomplished solely by friction engagement between the diaphragm, the cassette body 18 and the plunger 22, and no additional parts are required to provide this seal.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cassette for use in a volumetric infusion pump comprising:
    a cassette body having a volumetric chamber disposed therein, said chamber including an opening such that a piston of corresponding size is capable of sliding into the chamber through the opening, said cassette body further comprising a base surrounding said opening;
    a piston which is capable of reciprocating within said volumetric chamber;
    means for allowing fluids to enter and leave the volumetric chamber in response to the reciprocating movement of the piston;
    a diaphragm disposed between the piston and the volumetric chamber;
    a cuff formed around the periphery of said diaphragm for attachment to said cassette body; and
    a diaphragm casing twistingly engageable with said cassette body by inserting said diaphragm casing into a first position and rotating said casing approximately 90 degrees into a second position for securing said cuff of said diaphragm between said casing and said base of said cassette body.

2. A cassette for use in a volumetric infusion pump as defined in claim 1 wherein said diaphragm is generally cylindrical in shape having an enclosed upper end.

3. A cassette for use in a volumetric infusion pump as defined in claim 2 wherein the diaphragm is configured such that a friction engagement is obtained between the diaphragm and the piston such that the diaphragm and the piston move in unison.

4. A cassette for use in a volumetric infusion pump as defined in claim 2 further comprising a gap between at least a portion of the piston and at least a portion of the diaphragm casing such that the diaphragm can retract into said gap as the piston withdraws from the volumetric chamber.

5. A cassette for use in a volumetric infusion pump as defined in claim 1 wherein the diaphragm is constructed of an elastomeric material.

6. A cassette for use in a volumetric infusion pump as defined in claim 1 wherein said diaphragm provides a liquid tight seal between the volumetric chamber and the plunger.

7. A cassette for use in a volumetric infusion pump as defined in claim 1 wherein the means for allowing predetermined volumes of fluid to enter and leave the volumetric chamber comprises an inlet corridor, an outlet corridor, and a central corridor, said central corridor being in communication with the volumetric chamber at its lower end and in communication with the inlet corridor and the outlet corridor at its upper end, said upper end forming an intersection between the inlet corridor, the outlet corridor and the central corridor.

8. A cassette for use in a volumetric infusion pump as defined in claim 7 further comprising a two way valve disposed at the intersection between the inlet corridor, the outlet corridor and the central corridor.

* * * * *